United States Patent [19]

Fleischhacker et al.

[11] Patent Number: 5,165,421
[45] Date of Patent: Nov. 24, 1992

[54] HOLLOW LUMEN CABLE APPARATUS

[75] Inventors: Mark G. Fleischhacker, Minnetonka; Joseph F. Fleischhacker, Jr., Mound, both of Minn.

[73] Assignee: Lake Region Manufacturing Co., Inc., Chaska, Minn.

[21] Appl. No.: 555,899

[22] Filed: Jul. 20, 1990

Related U.S. Application Data

[63] Continuation of Ser. No. 102,878, Sep. 30, 1987, abandoned.

[51] Int. Cl.$^5$ .............................. A61B 5/00
[52] U.S. Cl. ...................... 128/772; 464/58; 604/282; 138/130; 74/502.5; 267/168
[58] Field of Search .............. 128/656-658, 128/772; 604/95, 264, 282; 29/435; 464/53, 58, 7; 138/130; 267/168; 74/502.5

[56] References Cited

U.S. PATENT DOCUMENTS

| 267,343 | 11/1882 | Harrison | 138/130 |
|---|---|---|---|
| 492,266 | 2/1883 | Browne | 464/58 |
| 1,228,439 | 6/1917 | Hotchkiss | 29/435 |
| 1,429,146 | 10/1922 | Karge | 138/130 |
| 1,808,193 | 6/1931 | Webb | 29/435 |
| 2,048,471 | 7/1936 | Sanford | 138/130 |
| 2,955,592 | 10/1960 | MacLean | |
| 3,552,384 | 1/1971 | Pierie et al. | 128/657 |

FOREIGN PATENT DOCUMENTS

0028115 8/1911 United Kingdom .................. 464/58

Primary Examiner—John D. Yasko
Assistant Examiner—Anthony Gutowski
Attorney, Agent, or Firm—Hugh D. Jaeger

[57] ABSTRACT

A hollow lumen cable is formed by helically winding inner and outer coils with the helices of each coil being in an abutting relationship and the outer coil inner peripheral diameter being less than the outer peripheral diameter of the inner coil. Preferably, each coil is multifilar. After the coils are wound, an unwinding force is applied to the outer coil and the inner coil is inserted into the outer coil to have its winding inclined opposite to that of the outer coil; and thence, the outer coil is allowed to contract to form an interference fit with the inner coil. The cable may be incorporated as part of a medical apparatus. For example, the cable distal end is connected to an implantable pump or other rotatable medical apparatus and the proximal end to a powered prime mover. A manually operated control member is attached to the cable proximal end portion, and the distal end to a medical sub-assembly such as a forceps or cutter; or as a part of a guide wire, or as part of a catheter to impart torque control. The cable is bendable about the tight radii and has a high torque transfer resolution while having a small cable outer diameter, a relatively long life, and has a hollow lumen in which there is no structure or through which fluid, wires or medical devices may pass.

4 Claims, 10 Drawing Sheets

HOLLOW LUMEN CABLE APPARATUS

This application is a continuation of U.S. Ser. No. 07/102,878, filed Sept. 30, 1987, entitled "Hollow Lumen Cable Apparatus" (now abandoned).

BACKGROUND OF THE INVENTION

A cable usable for incorporation in medical apparatus.

It is old to provide a cable by winding one or more strands of wire about a linear central wire in contact with the wire throughout at least a major part of the axial length of the central wire. However, with such prior art cables, the useful life is shortened due to fracturing of the central wire, particularly when it is of such relatively small diameters. Furthermore, such cables cannot be bent about such a relatively tight radii and still, satisfactorily transfer torque from one end to the other with high resolution due to the solid core wire taking a set. Additionally, it is hard to clean out all of the foreign material entrapped during the manufacture of the solid lumen helical cables.

Oldbergh U.S. Pat. No. 3,267,697 discloses a universal joint for automobiles that includes a plurality of multifilar spring units in a telescoped relationship. The inside diameter of the intermediate spring unit is slightly less than the outside diameter of the inner spring unit. During assembly, the inner unit is preloaded to cause radial contraction and after being inserted into the intermediate unit, it is allowed to expand. The radial intermediate coil is wound in the opposite direction from that of the winding of the inner and outer coils. Ruegg U.S. Pat. No. 25,543 and Hotchkiss U.S. Pat. No. 1,228,439 each disclose a flexible coupling member and a flexible shaft, respectively, each of which includes an intermediate coil wound in a direction opposite that of the radially inner and outer coils. Sperling U.S. Pat. No. 1,279,773 also discloses a flexible shaft having oppositely wound coils.

Lerwick U.S. Pat. No. 3,811,446 discloses an endarterectomy apparatus that includes an electric motor which drives a pair of springs that in turn drive the input shaft of a converter. The inner coil is multifilar and is enclosed by an outer helical spring. Wampler U.S. Pat. No. 4,625,712 discloses an intravascular blood pump drivenly connected by a flexible shaft to a support unit that is located outside of the human body.

Kline U.S. Pat. No. 3,749,086 discloses a guide wire having an outer spring coil that extends between the proximal and distal tips, and in two embodiments, an inner coil only in the distal end portion of the outer coil and in two embodiments, a wire core extends between the tips.

Each of Takahashi U.S. Pat. No. 4,178,810 and Sanagi U.S. Pat. No. 4,632,110 discloses a coil spring having forceps mounted on one end thereof, and a manipulating handle mounted on the other end. Auld U.S. Pat. No. 4,646,736 discloses transluminal thrombectomy apparatus having a shaft comprised of a 3 mil gold wire helically wound about a 4 mil stainless steel arbor for rotating a tip and being driven by a prime mover. Mac Lean U.S. Pat. No. 2,955,592 discloses a medical instrument having a sheath that includes an outer coil and an inner coil. Willson discloses a vascular tissue removing device that includes a single layer multistrand closely spaced helically wound coil of wire (U.S. Pat. No. 3,749,085).

Kensey et al U.S. Pat. No. 4,664,112 discloses a catheter bendable about a radius of curvature, e.g. 3", and having a working head rotated at a high speed by a drive assembly. In one embodiment, the drive assembly includes two interlaced helical wires having their distal ends joined to a cutting tip. The two wires are wound about a guide wire to rotate about a guide wire, having outside diameters of 0.01", and are loosely wound.

Kline U.S. Pat. No. 3,757,768 discloses a spring guide catheter wherein a plastic tube is heat shrunk over a coil spring, while O'Neil U.S. Pat. No. 4,145,247 discloses a pacer lead wherein a coil conductor is enclosed in an insulating layer.

Each of Samson et al U.S. Pat. No. 4,538,622 and Leary U.S. Pat. No. 4,545,390 discloses a PCTA guide wire that includes a main wire having a proximal cylindrical portion, a tapered intermediate portion, a cylindrical distal end portion of a smaller diameter than the proximal cylindrical portion, a helically wound coil having a proximal portion joined to the tapered portion, and a distal tip joined to one or both of the main wire distal end and the coil. In Samson, the coil includes two coil portions of different materials.

One of the problems encountered in the prior art is the lack of a very small diameter, highly flexible cable that has a relatively long life even when bent about relatively small radii for forming a part of the medical apparatus; for example, rotating or otherwise moving all or part of a medical device or medical subassembly and is medically clean. In order to overcome problems such as the above, as well as others, this invention has been made.

SUMMARY OF THE INVENTION

Hollow lumen cables that are usable for driving medical devices or mounting medical devices that includes a multifilar inner coil that in a non-assembled relaxed condition is of a given outer coil diameter, and a multifilar outer coil that in a non-assembled relaxed condition is of a given inner coil diameter which is smaller than that of the inner coil outer diameter. In an assembled condition, the inner and outer coils are oppositely wound with the outer coil inner peripheral surface being in an interference fit relationship with the outer peripheral surface of the inner coil. The cable may be used for forming a drive connection between a powered prime mover and a pump mountable in a human body, for driving an atraumatic tip, for having a manually manipulated handle mounted on one axial end and, for example, a forceps mounted on the opposite end, or for forming a part of a guide wire. Advantageously, the outer coil may be of an outer coil diameter of about 1/16" or less.

One of the objects of the invention is to provide a new and novel hollow lumen cable for use in the medical field. In furtherance of the above object, it is another object of this invention to provide a new and novel method of making such a cable. Another object of this invention is to provide a new and novel cable usable in the medical field that is of a relatively small outer diameter, and can form a drive connection that is rotatable at relatively high speeds with high torque resolution even when bent about a relatively tight radii of curvature, including through a circle, and is medically clean. Still another object of this invention is to provide new and novel guide wire means that incorporates the cable of this invention.

For purposes of this application, a "hollow lumen cable" relates to a cable wherein none of the strands of helically wound wires are wound around and in contact with a linear central wire.

BRIEF DESCRIPTION OF THE INVENTION

Figure 1:
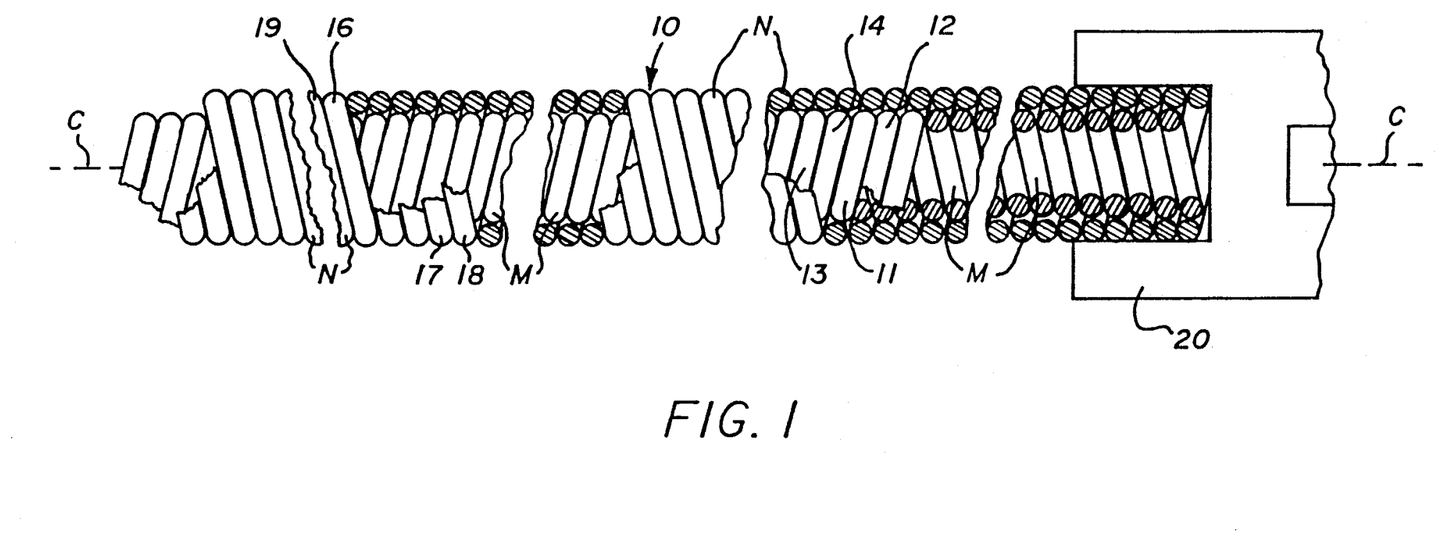
FIG. 1 is in part a side view, in part a cross-sectional view through the outer and inner coils, and in part a cross-sectional view through the outer coil, a side view of the inner coil of the cable of this invention, a cross-sectional view through a part of a connector or coupling, and a number of axial intermediate parts being broken away.
Figure 2:
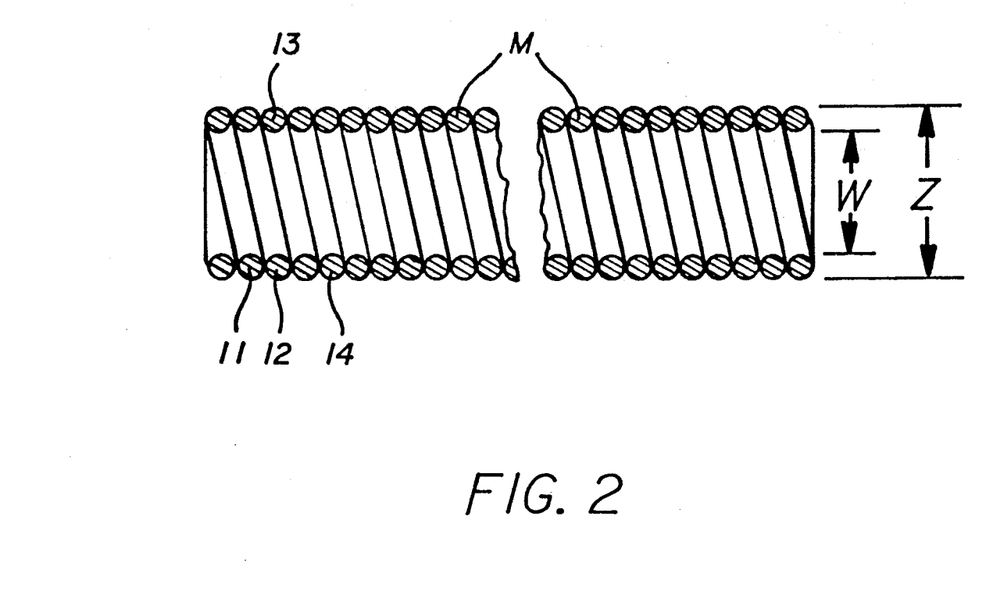
FIGS. 2 and 3 are fragmentary cross-sectional views of the inner coil and outer coil, respectively, in their relaxed non-assembled conditions.
Figure 3:
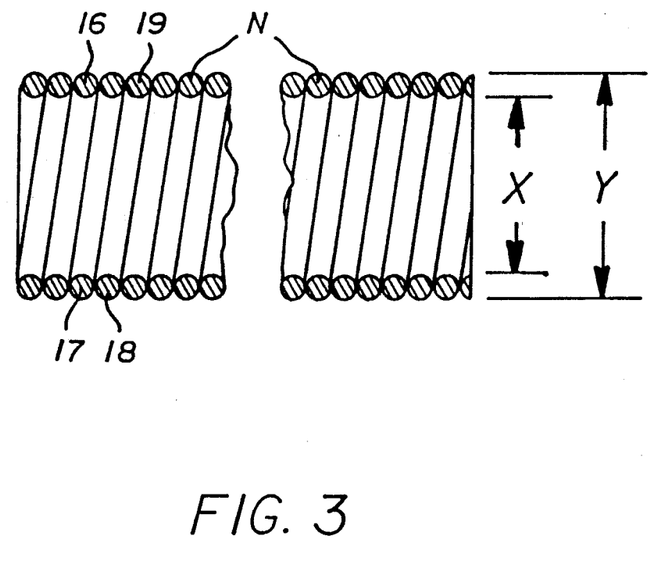

Referring to FIGS. 1-3, the hollow lumen cable of this invention, generally designated 10, includes an inner coil M made up of a single layer of multifilar helically wound coil of wires, preferably four wires 11, 12, 13 and 14 that each have convolution (helice) of one wire in contact with the adjacent convolution of two other wires. The inner coil is wound in a relaxed non-assembled condition having a coil inner peripheral diameter W and a coil outer peripheral diameter Z. The hollow lumen cable 10 also includes an outer coil N made up of a single layer of multifilar helically wound coil of wire, preferably four wires 16, 17, 18 and 19 that are wound in the opposite direction from the winding of the inner coil, and likewise, has adjacent wire convolutions in contact with one another. The outer coil is wound in a relaxed non-assembled condition having a coil inner peripheral diameter X and a coil outer peripheral diameter Y. For example, the inner coil outer peripheral diameter, in a non-assembled condition, may be about 0.002" greater than the outer coil inner peripheral diameter in a non-assembled condition.

For medical uses, prior to winding each of the coils, each strand of wire is cleaned to remove any foreign material on the wire strands and then the desired number of cleaned strands are simultaneously wound to form the respective coil. After the inner and outer coils have been formed, each of the inner and outer coils are cleaned to remove any foreign material on the coils. Subsequent to cleaning the coils, the coils are assembled as set forth below and then the assembled cable is cleaned. Further, if after forming the cable, a coupling, medical device or other structure is joined to the cable, the cable, with other structure joined thereto, is cleaned. Each of the cleaning steps are carried out such that strands of wire, coils and cable are medically or surgically clean.

In order to assemble the cable, the outer coil is partially unwound by applying an unwinding force to increase the coil inner peripheral diameter. Then the inner coil is inserted into the partially unwound outer coil, and thence, the unwinding force that was applied to the outer coil is released. The axial central part of the outer coil starts to shrink first to form an interference fit with the inner coil and continues to shrink its outer coil diameter toward the outer coil opposite ends, whereby there is obtained an interference fit throughout the entire axial length of the cable. All of the helices of each of the coils in the assembled condition of the coils are of substantially the same inner and outer diameters throughout the axial lengths of the coils, while the inner and outer coils are of substantially the same axial lengths. That is the helices of each coil is of substantially the same radial spacing from the respective coil central axis C—C.

When forming the cable in the manner set forth herein, it is not necessary to solder or otherwise join the ends of the strands of wire of each coil at either axial end, or the coils to one another to maintain the cable in an assembled condition (no unwinding of the strands). Rather, the cable may be shipped for later incorporation with other components or for use. Even if the cable is cut into, for example, two axial half sections, the strands at either end of the half sections will not unwind. This is in contrast to prior art solid wire helically wound cables wherein the wire is in tension in an abutting relationship to the central core wire and not welded or soldered at various axial positions to the central core wire. In hollow lumen cables there is no interference fit between radially adjacent coils throughout their axial lengths. Depending upon the use to be made of the cable of this invention, the distal ends of the strands of wire of the inner coil and the outer coil may be suitably joined to one another by, for example, brazing, or soldering to round off sharp ends to a suitable coupling member 20 such as shown in FIG. 1, or to a member for connecting the distal end to other structure. Likewise, the proximal ends of the strands of wire of the coils may be joined. The coupling member 20 that is shown in FIG. 1 is particularly suitable for forming a keyed connection to a shaft that is to be driven or to provide a driving force. Due to the interference fit of the inner an outer coils throughout their axial lengths, there is substantially a 1 to 1 transmittal of torque from one end of the cable to the other regardless of the direction of rotation of the cable.

If one were to exert a winding force to the inner coil to reduce its outer coil diameter or leave the inner coil on a mandrel in a non-relaxed condition, then insert the reduced diameter or non-relaxed inner coil into the outer coil, and thence release the winding force that was applied to reduce the inner coil outer diameter or allow the inner coil to expand on the mandrel, the inner coil would expand its outer diameter from its axially opposite ends toward the center. However, due to the axially opposite ends expanding first, the axially opposite ends form an interference fit with the outer coil and, as a result, the inner coil stops expanding before the inner coil axially intermediate portion has fully expanded. During use of the thus formed cable the inner coil gradually turns relative to the outer coil and strands of the inner coil become misaligned with reference to the outer coil. This results in the cable failing in a substantially shorter period of time than when the cable is made such as described in the preceding two paragraphs.

Figure 4:
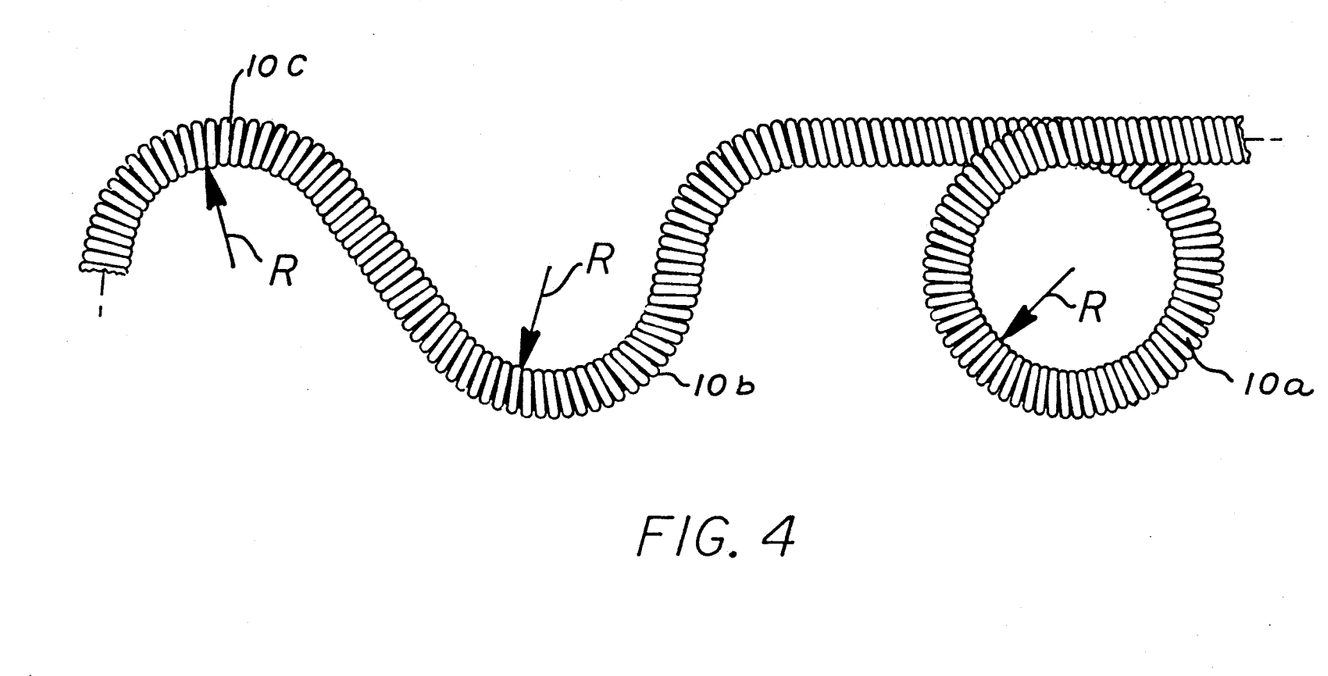
FIG. 4 is a side view of a part of an axial length of the cable of this invention for purposes of indicating the flexibility of this invention.

By assembling through partially unwinding the outer coil and allowing it to contract after the inner coil has been inserted, the hollow lumen cable 10 may be made of an outer diameter of about 1/16" or less and bent through, for example, a circular configuration portion 10a of a radius of curvature R of, for example, about 1" and/or "S" curved portions 10b, 10c radii of curvature such as indicated (see FIG. 4). Such a cable may be, for example, 5 to 15 ft. long and have one end coupled to a motor and an opposite end coupled to a pump to be rotated at, for example, 20,000 rpm, and the part of the cable forming the circular portion being spaced from the coil parts completing the circular configuration being spaced less the cable outer diameter. That is, the cable may be extended through a very tortious path when being used without taking any significant set such as occurs with solid lumen cables. The cable may be passed through tortious bends such as found in cardiac and vascular systems and rotated at relatively high speeds if located within a catheter.

Figure 5:
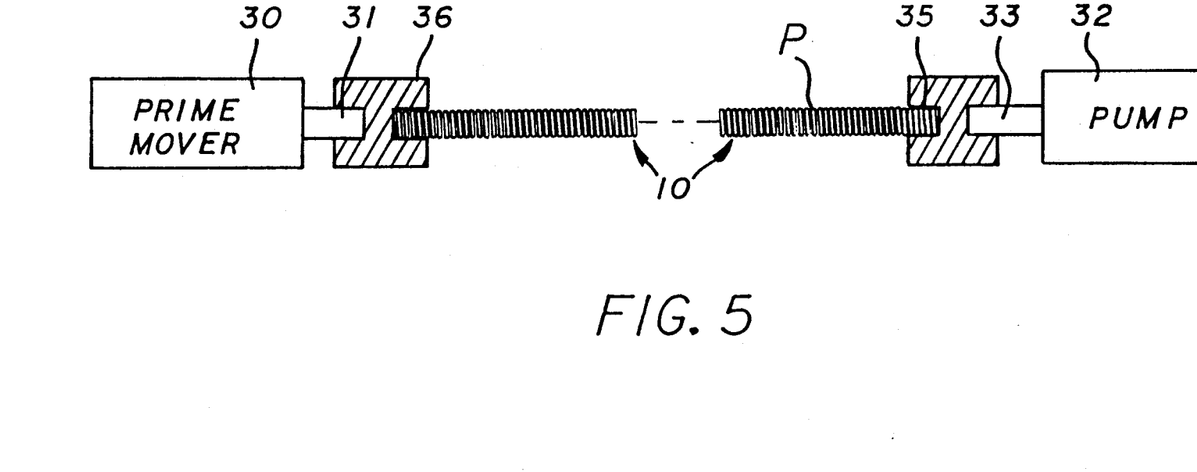
FIG. 5 is a side view of a power driven medical apparatus that includes a prime mover, a heart pump and the cable of this invention.

The hollow lumen cable 10 may be incorporated in medical apparatus P to form a drive connection from a prime mover (motor) 30 having a drive shaft 31 to, for example, a heart pump 32 that has a drive shaft 33 or another type of medical device, for example, a cylindrical atraumatic tip, such as disclosed in U.S. Pat. No. 4,646,736 to Auth. If the cable is to be used to form a drive connection, a suitable connector (coupling) 35 is soldered or otherwise fixed to the distal ends of the strands of the coils, and is adapted to be removably connected to the motor shaft while a suitable connector (coupling) 36 is similarly fixed to the proximal ends of the strands of the wire of the cable coils. The couplings are keyed or otherwise attached to the shafts 31 and 33. The pump and motor may be of the type disclosed in and used in the manner disclosed in U.S. Pat. No. 4,624,712 to Wampler, and thus it is believed there is no need to further disclose the operation of medical apparatus P.

In place of members 32, 33 and 35 as previously described, the hollow lumen cable 10 may be extended into a catheter tube (not shown) to drive a working head or cutter member (not shown) mounted by the catheter tube distal end portion for high speed rotation such as disclosed with reference to FIG. 5 of Kensey—U.S. Pat. No. 4,664,112. That is, the hollow lumen cable 10 may be driven by prime mover (motor) 30, and advantageously used in place of the two helically wound, interlaced wires to drive the working head of Kensey, with a guide wire extended into the lumen of hollow lumen cable 10 or without a guide wire extended into the lumen.

Figure 6:
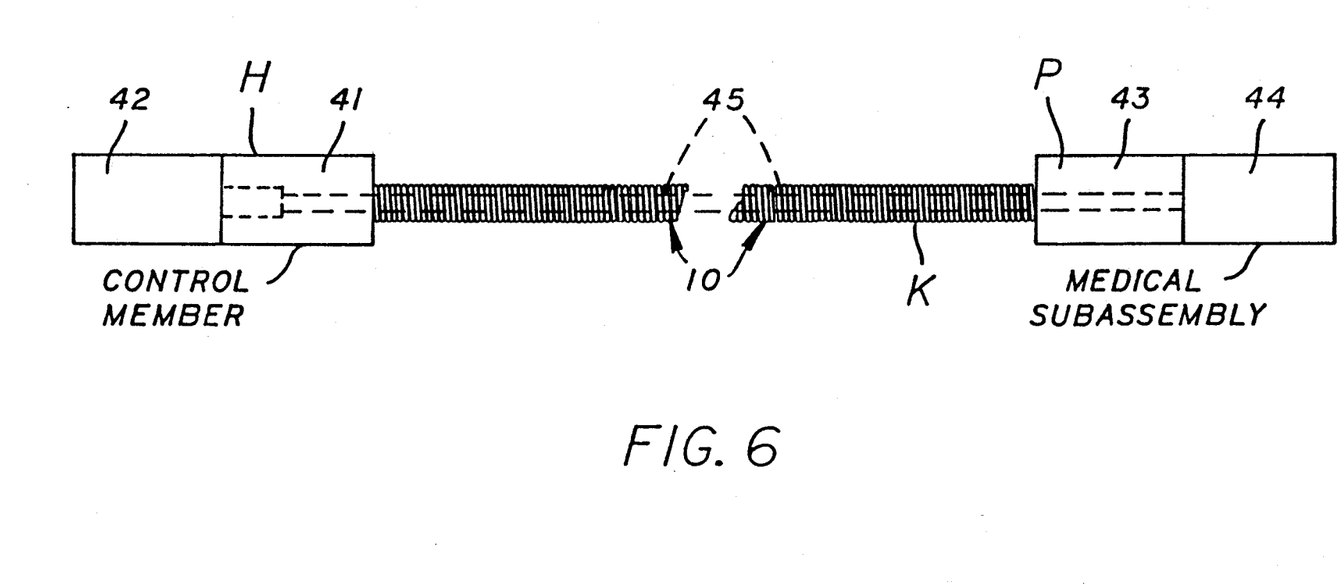
FIG. 6 is a side view of a manually operated medical apparatus that includes a control member, a medical sub-assembly, for example a cutter or forceps and the cable of this invention mounting the control member and medical sub-assembly, the control member and medical sub-assembly being diagrammatically illustrated; and, FIGS. 7-10 are cross-sectional views of four embodiments of guide wires incorporating the cable of this invention with the axial intermediate portions being broken away.

Referring to FIG. 6, the medical apparatus K includes a hollow lumen cable 10 that has its proximal end portion fixedly attached to the manually operated control member H while the distal end portion mounts a medical sub-assembly D. The control member and medical sub-assembly being diagrammatically illustrated. The medical sub-assembly device D may be of a type that only moves when the cable moves and does not have one operative part movable relative to another part. That is, the medical sub-assembly device may be a tissue scraping tool such as shown in FIG. 1 of U.S. Pat. No. 3,749,085 to Willson et al, and welded or attached by a suitable connector part 43 to the distal end portions of the strands of the cable coils while the control member may be a single part member for rotating and/or pushing the cable through a catheter. The manually operated control member H may include a manipulator portion 42 that corresponds to element 29 of Willson, a finger grip portion 41 corresponding to portion 30 of Willson, and a medical sub-assembly cutter device D that corresponds to the scraper mechanism shown in FIG. 1 of Willson and mounted on the distal ends of the strands of wire of the cable by the scraper mechanism being soldered or brazed to a connector (not shown), which in turn is suitably fixed to the distal end of the hollow lumen cable 10. By using the hollow lumen cable 10 there is no need to provide a core wire such as provided in Willson.

As another alternative, the medical apparatus K may be of a type that the medical sub-assembly D may be a forceps or cutter having one or more medical device parts 44 movable relative to another suitable connector part 43, which is fixedly attached to the cable wire distal ends. The movable medical device part (parts) 44 may be moved relative to suitable connector part 43 by a core member 45 which extends through the hollow lumen cable 10 and is of a substantially smaller diameter than the inner diameter of the inner coil M. The proximal ends of the cable coils are mounted to the finger grip portion 41 of the control member H while the proximal end of the core member 45 is mounted to the manipulator portion 42 of the control member H. The manipulator portion 42 is manually movable relative to the finger grip portion 41 for moving the core member 45 and thereby, the medical device part 44 relative to suitable connector part 43. The medical apparatus K may be of the general nature disclosed in U.S. Pat. No. 4,178,810 or U.S. Pat. No. 4,632,110 wherein the medical device part 44 is forcep cups, suitable connector part 43 a tip mounting the cups and being mounted on the distal end portion of the hollow lumen cable 10, the cable taking the place of the coil sheath of these patents, and the core member 45 being connected to the manipulator portion 42 for operating the medical device part 44. That is, the hollow lumen cable 10 may be used in place of the coil sheath of U.S. Pat. No. 4,632,110 and have the distal ends of its strands attached to the tip which mounts the forcep cups. It is believed that in view of the above description, and if necessary, a reference to either of U.S. Pat. No. 4,178,810 or U.S. Pat. No. 4,632,110 it is not necessary to further describe the operation of this alternative form of medical apparatus K.

Figure 7:
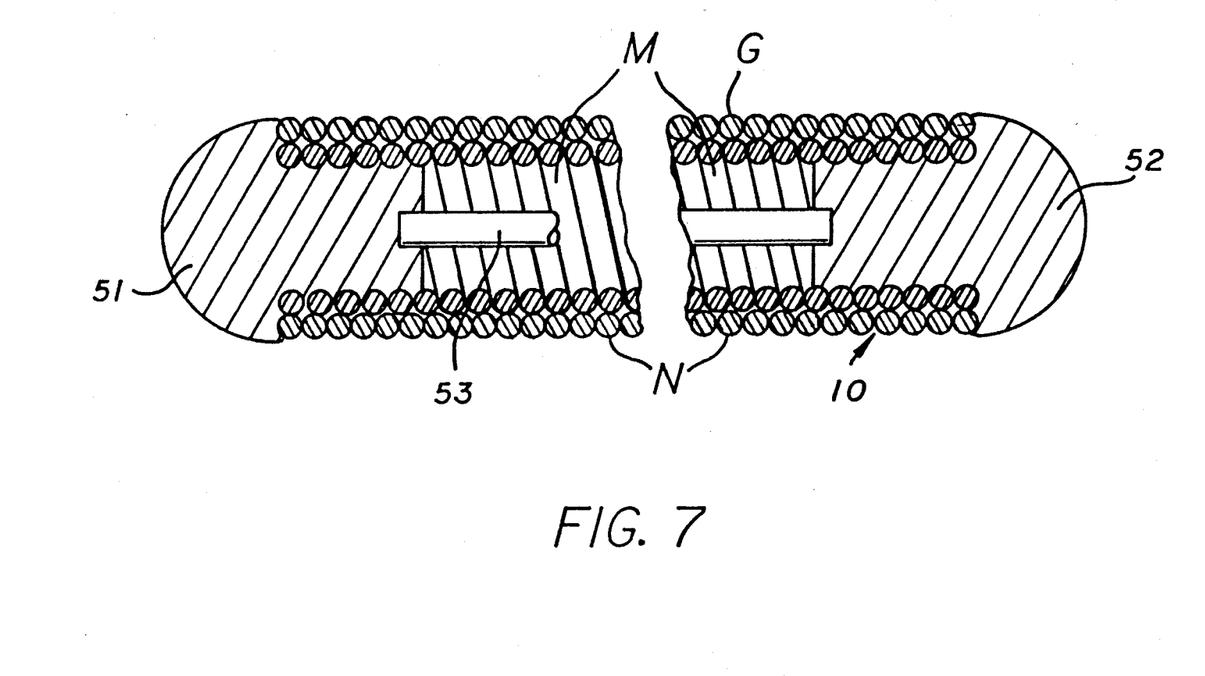

Referring to FIG. 7, the medical apparatus G comprises a guide wire that comprises a hollow lumen cable 10 having a proximal guide wire tip 51 attached to the proximal ends of the cable wires, for example by welding or soldering, while a distal guide wire tip 52 is similarly fixedly attached to the distal ends of the cable wires. A core wire (main wire) 53 is optionally extended through the cable to have its opposite ends joined to the adjacent proximal guide wire tip 51 and distal guide wire tip 52. The diameter of the core wire being much smaller than the inner diameter of the inner coil M. Because of the torque transmission capabilities of the cable of this invention, there is no need to solder various axial intermediate parts of a core wire (if provided) in order to properly transfer torque from the guide wire proximal tip to the distal tip, if such tips are provided at axially opposite ends of the guide wire as shown in FIG.

7. The medical apparatus G may be used in a conventional manner, for example, see U.S. Pat. No. 3,749,086.

Figure 8:
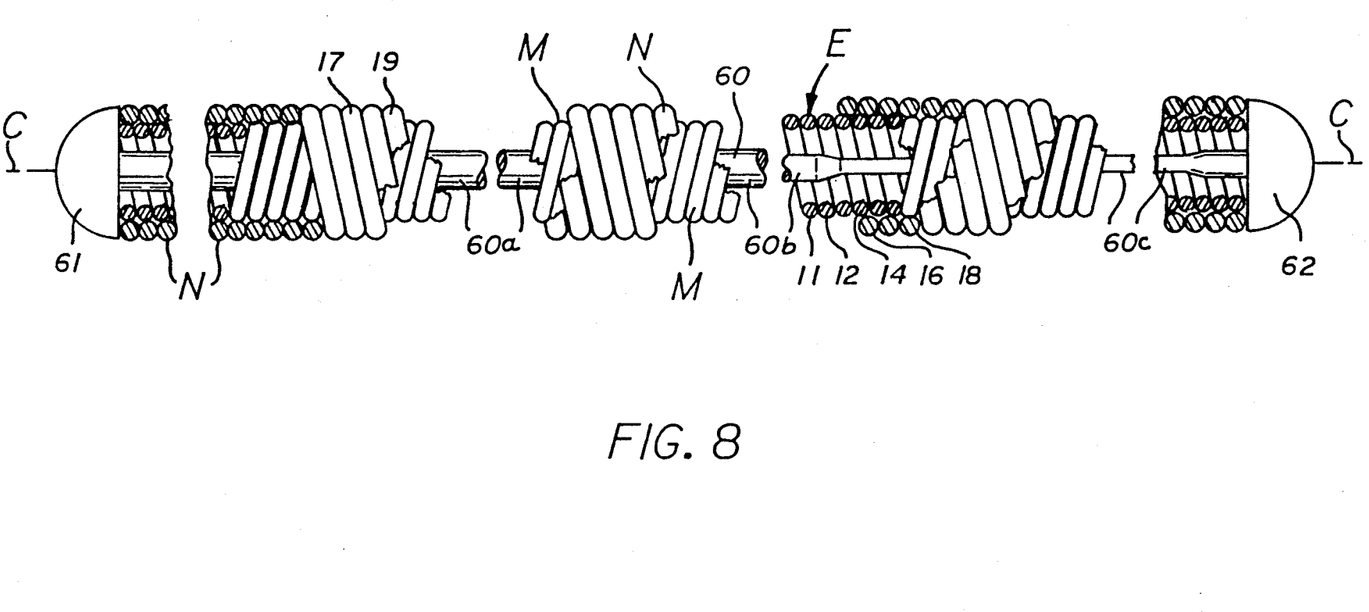

Referring to FIG. 8, a second embodiment of the guide wire of this invention, generally designated E, is similar to that disclosed with reference to FIG. 7, other than for the main wire core wire or member 60 and second embodiment E being a high strength guide wire. The main wire core wire assembly 60 has a proximal cylindrical portion 60a having its proximal end joined to the proximal tip 61, which in turn is joined to the cable proximal end portion. The distal end of the main wire 66 is integrally joined to the major base end of the frustoconical axial intermediate (tapered) portion 60b of the main wire 66 while the distal end of the intermediate portion is integrally joined to the distal cylindrical portion 60c of the main wire 66, portion 60c, in turn, being joined through a main wire distal terminal end portion 60d. The main wire distal terminal end portion 60d may be flattened and is joined to the cable distal end by the distal tip (bead) 62.

Figure 9:
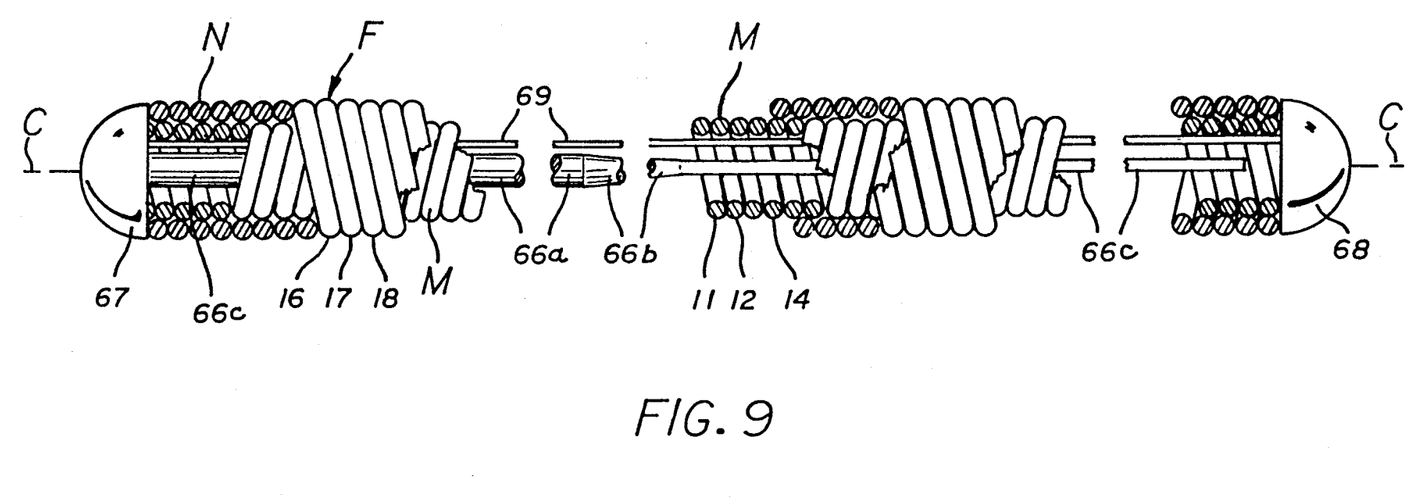

Referring to FIG. 9, the third embodiment of the guide wire of the invention, generally designated F, is similar to that disclosed with reference to FIG. 8. That is, the main wire 66 of the third embodiment F has a cylindrical portion 66a, an axially intermediate (tapered) portion 66b and a cylindrical portion 66c that corresponds to proximal cylindrical portion 60a, frustoconical axial intermediate (tapered) portion 60b and distal cylindrical portion 60c, respectively. The main wire proximal end is joined to the proximal ends of the hollow lumen cable 10 (inner coil M and outer coil N) by a proximal tip 67, while a distal tip 68 is joined to the distal ends of the coils with the main wire 66 extending through the hollow lumen of the cable. However, the distal terminal end of cylindrical portion 66c terminates short of the distal tip 68. A safety wire 69 is provided within the hollow lumen of the cable and has its proximal and distal ends joined to the proximal and distal tips respectively.

Figure 10:
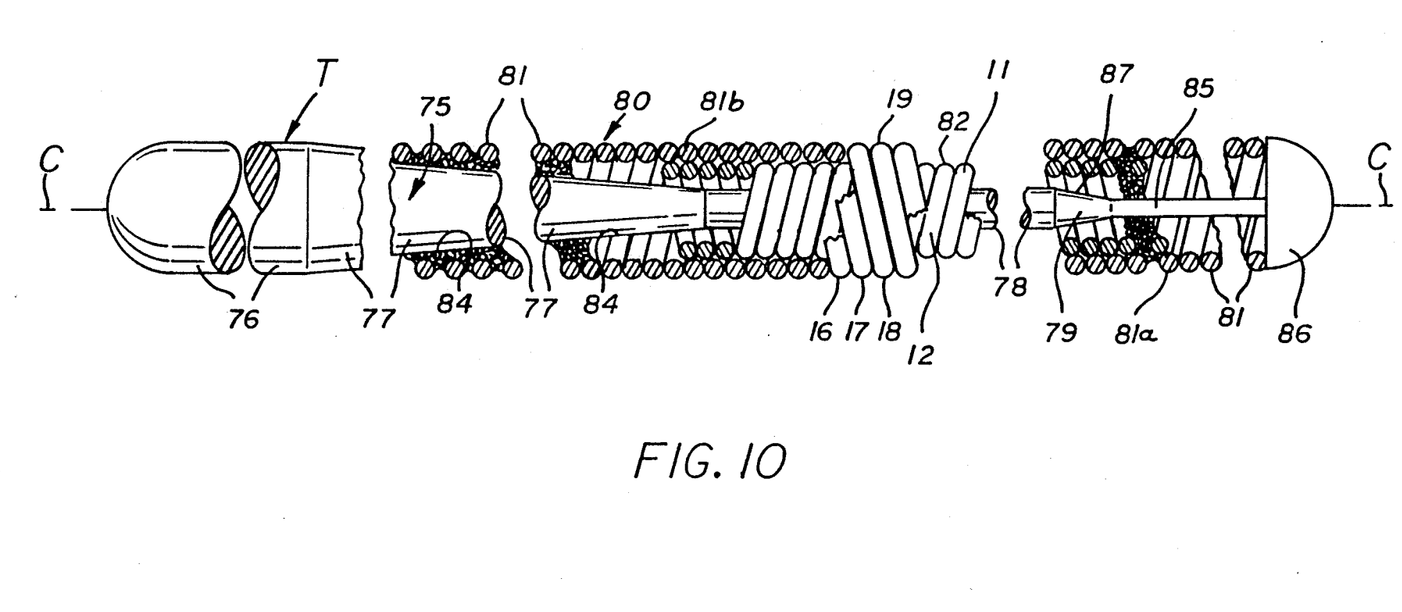

Referring to FIG. 10, there is shown a PTCA guide wire of this invention, generally designated T, that includes a main wire 66, generally designated 75, which has a proximal cylindrical portion 76 where at its distal end is integrally joined to the major base of the first frustoconical tapered (axially intermediate) portion 77, while the minor base of the first frustoconical tapered (axially intermediate) portion 77 is integrally joined to the second cylindrical portion 78. The second cylindrical portion 78 is of a substantially smaller diameter than that of proximal cylindrical portion 76.

As shown in FIG. 10, a cable, generally designated 80, is a modified form of the hollow lumen cable 10 which is formed in the same manner as the hollow lumen cable 10 except that the outer coil 81 is of a longer axial length than the inner coil 82. The proximal end portion of the inner coil 82 and the radially adjacent part of the outer coil 81 are brazed or otherwise suitably joined to the first frustoconical tapered (axially intermediate) portion 77 at 83 while the proximal end portion of the outer coil 81 likewise, is suitably joined at 84 to the tapered portion. The taper of the tapered portion, the axial distance of the outer coil, extends more closely adjacent to the proximal terminal end of the main wire than the inner coil, and the axial spacing of the terminal ends of the coils is such that the outer diameter of the outer coil is substantially the same as that of the proximal cylindrical portion and is of substantially the same outer diameter throughout its axial length. The inner diameter of the inner coil is sufficiently greater, leaving an annual space between the inner coil and the cylindrical portion. Further, the inner coil, throughout its axial length, is in interference fitting relationship with the outer coil.

The second cylindrical portion 78 is integrally joined to the major base of the second frustoconical portion 79, which in turn has a minor base integrally joined to the proximal end of the distal end portion 85. The distal end portion 85 is joined to the guide wire distal tip. The distal end portion 85 may be circular, cylindrical or rectangular in transverse cross section. The distal end portion 85 is of a substantially smaller transverse cross-sectional area than that of the second cylindrical portion 78 which in turn is a substantially smaller diameter than that of proximal cylindrical portion 76. The distal end of the inner coil and the radially adjacent part of the outer coil is brazed or otherwise suitably joined at brazing 87 to either one or both of the second frustoconical portion 79 and/or distal end portion 85, advantageously adjacent to the juncture of the second frustoconical portion 79 and the distal end portion 85. The axial length of the outer coil, in a distal (forward) direction, may be sufficiently greater than that of the inner coil to extend from the brazing 87 to the distal tip 86 to be joined thereto. That is, the outer coil may have a coil portion 81a joined to and extended from brazing 87 to the distal tip 86, and integrally joined with portion 81b as one unitary coil. However, advantageously the distal terminal ends of the inner and outer coils of cable 80 are of substantially the same axial spacing from the distal tip 86 and a second coil portion 81b; which may or may not be of the same material as the second coil portion 81b and may or may not be multifilar; and has its distal end joined to the distal tip and its proximal end joined to brazing 87. In such an event, the second coil portion 81b in interference fitting relationship with the radially adjacent parts of coil 80.

In place of the main wire 75, having intermediate portions 77-79 as described above, portion 77-79 may be modified such that the portion 77-79 may be of the same diameter throughout its axial length as the second cylindrical portion 78 and integrally joined to the proximal cylindrical portion 76 to form an annular radial shoulder with both the inner and outer coils extending in a rearward direction to have their proximal ends abut against or be closely adjacent to such a shoulder, and be brazed or otherwise suitably joined to one or both of the first frustoconical (axially intermediate) portion 77 and the modified intermediate portion without the coils otherwise being joined to the main wire, except at brazing 87. The outer diameter of the outer coil with the modified intermediate portion would be substantially the same as that of the first frustoconical tapered (axially intermediate) portion 77.

It is to be noted that the outer coil of cable 80 may have its proximal terminal end radially adjacent to the inner coil proximal terminal end, and in such an event, brazing or other material may be provided on the tapered portion axially between the cylindrical portion 66a and the proximal coil terminal ends to avoid an abrupt change of the coil distal terminal ends and the radially adjacent part of the main wire tapered portion.

As an example of the guide wire of this invention, but not otherwise as a limitation thereof, the main wire 66 of the third embodiment F of FIG. 9 may be of a length of about 50–400 cm, the axially intermediate (tapered) portion 66b of a length of about 3.5 cm, the cylindrical portion 66c of a length of about 3.5 cm and of a diameter of about 0.004" or 0.005", and the cylindrical portion 66a of a diameter of about 0.010"-0.018". Similarly, as an example of the embodiment of FIG. 10, the length of the main wire may be about 180 cm, the proximal cylindrical portion of a diameter of about 0.012"-0.018", the first frustoconical tapered (axially intermediate) portion 77 of a length of about 2 cm, the second cylindrical portion 78 of a length of about 28 cm and a diameter of about 0.008", the second frustoconical portion 79 of a length of about 2 cm and if circular, a diameter of about 0.003" (advantageously flattened to have a major transverse dimension substantially less than the inner diameter of the inner coil) and the first coil portion (third coil) 81a of an axial length of about 2 cm. Thus, the axial length of the proximal cylindrical portion 76 is substantially greater than the combined axial length of portions 77-79 and 85. The outer diameter of each of the outer coils of the guide wires of this invention are less than 1/16", whereby the guide wire incorporating the cable of this invention is suitable for use as a vascular guide wire. The diameter and length of the various parts of the guide wire would depend upon the particular use to be made of the guide wire.

A further use that may be made of the cable is to have electric leads (not shown) extended through the hollow lumen cable 10 or to be used in place of each of the coil springs such as disclosed in U.S. Pat. No. 4,154,247. Still another use is that fiber optical bundle (light guide), not shown, may be located in the hollow lumen of the hollow lumen cable 10 in a fixed relationship to the cable, or may be pushed into the cable after the cable has been moved to the desired location in a body vessel. Another use is to incorporate the hollow lumen cable 10 as part of a catheter, wherein the cable is embedded in or surrounded by a plastic sheath (not shown) which is in fixed axial relationship to the cable. For example the cable may be used in place of the coil spring in a catheter such as disclosed by U.S. Pat. No. 3,757,768 to Kline.

The cable of this invention is of a particular benefit for use in vascular vessels wherein it is desired to have a cable as part of a medical apparatus that has an outer cable diameter of about 1/16" or less. Advantageously, the wires of the coils are of a diameter of about 0.001"-0.010", and as an example of this invention and not otherwise as a limitation thereon, the outer coil, in its relaxed non-assembled condition, has an outer coil outer diameter Y of about 0.038", an inner diameter X of about 0.028", and the inner coil N in its relaxed non-assembled condition has an inner coil outer diameter Z of about 0.030". With coils of dimensions set forth in the preceding sentence, there would be about a 0.002" interference fit. Cables of this invention may be of varying lengths, for example, of any length of about up to 14', and advantageously an interference fit of about 0.002"-0.010", depending upon the particular use.

Each strand may, in cross section, be round, ribbon shaped or of another desired cross section. For medical uses, advantageously each strand of wire is made of a material able to have a spring temper of a diameter of about 0.002-0.010", has a tensile strength of about 100,000-400,000 psi, and preferably 150,000-400,000 and is made of a metallic material suitable for use in a human body, for example, stainless steel, MP-35, or other metals or metal alloys containing one or more of, for example, tungsten, platinum, cobalt, nickel or other precious metals.

Although each coil has been described as being made of four wires, it is to be understood that each coil may be made of 2 or more metal wire strands. Further, the cable has been described as being made of two coils. However, the cable may be made of three or more coils in concentric relationship. For example, there may be provided a third coil (not shown) that is multifilar and wound to, in a relaxed non-assembled condition, a coil inner peripheral diameter that is somewhat smaller than the outer peripheral diameter of the assembled inner and outer coils, for example, about 0.002"-0.010". After the inner and outer coils have been assembled, an unwinding force is applied to the third coil to radially expand it sufficiently so that the assembled inner and outer coils can be inserted into the third coil; and after the inserting step, the unwinding force is removed to allow the third coil to contract to form an interference fit with the outer coil N. Now the cable is made up of three coils with the third coil being the outer coil, outer coil N the intermediate coil and inner coil M the inner coil with outer coil N being wound in the opposite direction from that of the third coil and the inner coil M. It is to be understood that the strands of wire are cleaned before forming the third coil, that the third coil is cleaned before the insertion step, and that the assembled three coils are also cleaned.

What is claimed is:

1. Guidewire system for medical procedures consisting of:
   a. a first helically wound coil having a coil central axis;
   b. a second helically wound flexible coil wound in an opposite direction with adjacent convolutions in contact and in an interfering fit relationship with said first helically wound coil such that the inner and outer diameters of said first helically wound coil are consistent along the full length of said first helically wound coil, and the inner and outer diameters of said second coil are consistent along the full length of said second coil from a distal end to a proximal end, each of the helices of said first and second coils having substantially the same radial spacing from said coil central axis for control of said coils; and,
   c. said first helically wound coil has outer diameter Z and said second helically wound coil has an inner diameter X such that in a non-assembled condition, Z is about 0.002 inches greater than X.

2. Guidewire system for medical procedures according to claim 1 further consisting of:
   a hollow lumen through said second helically wound flexible coil.

3. The guidewire system of claim 1, wherein said first and second helically wound coils comprises a hollow lumen cable, and wherein said interfering fit allows for a substantially 1 to 1 transmittal of torque from said promixmal to said distal end upon rotation of said cable, regardless of the direction of said rotation.

4. The guidewire system of claim 1, wherein said first and second helically wound coils comprise a hollow lumen cable, said cable having an outer diameter of about 1/16 inches or less.

* * * * *